United States Patent
Kawai et al.

(12)

(10) Patent No.: US 6,855,747 B2
(45) Date of Patent: Feb. 15, 2005

(54) METHOD OF PRODUCING ION SENSITIVE FILM FOR ION SENSOR

(75) Inventors: Tadashi Kawai, Tokyo (JP); Hirohisa Yoshida, Kanagawa (JP); Tokuo Mizuno, Tokyo (JP); Atsuro Tonomura, Tokyo (JP); Naoki Aota, Saitama (JP)

(73) Assignees: JEOL Ltd., Tokyo (JP); JEOL Engineering Co., Ltd., Tokyo (JP)

( * ) Notice: Subject to any disclaimer, the term of this patent is extended or adjusted under 35 U.S.C. 154(b) by 60 days.

(21) Appl. No.: 10/329,041

(22) Filed: Dec. 23, 2002

(65) Prior Publication Data

US 2003/0166736 A1 Sep. 4, 2003

(30) Foreign Application Priority Data

Dec. 28, 2001 (JP) ........................................ 2001-399793

(51) Int. Cl.[7] .............................. C08F 2/46; C08F 12/28
(52) U.S. Cl. ...................... 522/150; 522/151; 522/152; 522/153; 522/154; 522/173; 522/174; 522/175; 522/179; 522/178; 522/181; 522/182; 522/193; 204/418; 526/310; 526/290; 526/291; 526/301.1; 526/307; 526/318.1; 526/346; 526/317.1; 521/25; 521/28
(58) Field of Search ................................. 522/150, 151, 522/152, 153, 154, 173, 174, 175, 178, 179, 181, 182, 183; 204/418; 526/310, 290, 291, 301.1, 307, 318.1, 317.1, 346; 521/25, 38

(56) References Cited

U.S. PATENT DOCUMENTS 5,240,586 A * 8/1993 Moore et al. ................ 204/418
6,410,672 B1 * 6/2002 MacDonald et al. ........ 526/310

FOREIGN PATENT DOCUMENTS

JP          2504513          4/1996

* cited by examiner

Primary Examiner—James J. Seidleck
Assistant Examiner—Sanza L. McClendon
(74) Attorney, Agent, or Firm—Webb Ziesenheim Logsdon Orkin & Hanson, P.C.

(57) ABSTRACT

There is disclosed a method of easily producing a long-lived ion sensitive film having excellent durability and used in an ion sensor. The method starts with preparing a monomer mixture consisting chiefly of monomer units including a functional group and a second group of bonded atoms. The functional group has a function of identifying a certain chemical substance. The second group can become an active species that induces a polymerization or bridging reaction by being irradiated with an electron beam or radiation. Then, the monomer mixture is irradiated with the electron beam or radiation in a low energy range. Thus, the monomer mixture is polymerized.

13 Claims, 2 Drawing Sheets

METHOD OF PRODUCING ION SENSITIVE FILM FOR ION SENSOR

BACKGROUND OF THE INVENTION

1. Field of the Invention

The present invention relates to a method of producing an ion sensitive film used in an ion sensor (especially, an ion selective film) that is employed to measure the activity of ions within a liquid solution.

2. Description of Related Art

In recent years, ion sensors (especially, ion selective electrodes) for medical applications have been vigorously used to quantify ions (e.g., sodium, potassium, and chlorine ions) dissolved in a liquid within a living organism, such as blood or urine.

An existing ion sensor is shown in FIG. 1 and comprises a sensor (electrode) body 1 and an ion sensitive film 4 fixed to the front-end surface of the body 1. The inside of the body 1 is filled with an internal electrolyte 3. An internal electrode 2 made of silver chloride is immersed in this internal electrolyte.

Referring next to FIG. 2, this ion sensor, indicated by numeral 5, is immersed in a sample solution 6 together with a salt bridge 7. On the other hand, a reference electrode 9 is immersed in an aqueous solution 10 of saturated potassium chloride together with the salt bridge. The potential difference between both electrodes is read by an electrometer 8. Using a reference sample having a known concentration as an object to be measured, the electromotive force is measured, and a calibration curve is created. The ion concentration of the sample under investigation is found by comparing the electromotive force produced by the sample against the calibration curve.

The performance of such an ion sensor also depends on the performance of the used ion sensitive film. Known ion sensitive films used for ion sensors include (a) a film produced by preparing a film support material made of polyvinylchloride and mixing an ion sensitive material into the film support material together with a plasticizer, (b) an ion-exchange film, and (c) a "film-like substance" (disclosed in Japanese Patent No. 2504513) consisting of a polymer having a quaternary ammonium group having a certain structure.

However, the ion sensor using the ion sensitive film of the type (a) above has the disadvantage that the electrode life is short, because the ion sensitive material within the film gradually dissolves into the liquid solution.

The ion sensor using the ion sensitive film of the type (b) has a short life because ionic groups are introduced into a polymer by covalent bonding, the polymer forming a film. It has been pointed out, however, that the film is an ion-exchange film generally used for electrolytic purposes and so if the film is used as an ion sensitive film in an ion sensor, the film is affected greatly by interfering ions.

In the ion sensitive film of the type (c) as disclosed in the above-cited Japanese Patent No. 2504513, a straight-chain polymer is formed by polymerizing monomers having a quaternary ammonium group of a certain structure. Thus, the film shows excellent response to chlorine ions and good waterproofness. The ion selective electrode has a long life and can measure chlorine ions with high sensitivity stably.

The ion sensitive film of the type (c) is formed by normal heating radical solution polymerization using a radical polymerization starter and, therefore, limitations are placed on the degree of polymerization. In addition, molecular weights are broadly distributed. Therefore, it can be said that there remains room for improvements of durability and life. In addition, in such normal radical solution polymerization, it takes a long polymerization reaction time to increase the reaction rate. Furthermore, unreacted monomers remain. Additionally, it is laborious to refine the reaction mixtures.

SUMMARY OF THE INVENTION

We have discovered that a long-lived ion sensitive film having a high degree of polymerization, excellent durability, and a narrow range of molecular weights can be formed by preparing a monomer mixture and polymerizing the mixture by irradiating it with an electron beam or radiation in a low energy range. The monomer mixture consists chiefly of monomer units including a functional group having an identification function and a second group of bonded atoms capable of becoming an active species that induces a polymerization reaction by being irradiated with an electron beam or radiation. Furthermore, we have discovered that an ion sensitive film which is used in an ion sensor and which does not need to be refined can be obtained directly from a film-like monomer mixture, the monomer mixture reaching a high reaction rate in a quite short reaction time.

Other objects and features of the invention will appear in the course of the description thereof, which follows.

DESCRIPTION OF THE PREFERRED EMBODIMENTS

Monomer units used in the present invention have a functional group having a function of identifying a certain chemical substance. No limitations are imposed on this functional group, as long as the functional group can bond, directly or via a necessary connecting group, to a second group, such as vinyl group or allyl group, that can become an active species inducing a polymerization or bridging reaction by being irradiated with an electron beam or radiation.

Examples of such a functional group include functional groups having crown ether structure, valinomycin structure, calixarene structure, porphyrin structure, organotin structure, organomercuric structure, and cyclic polyamine structure, anion-exchange groups such as quaternary ammonium salts, and cation-exchange groups, such as sulfonic group and carboxyl group.

Examples of the certain chemical substance that can be identified by these functional groups include cations (such as sodium ions, potassium ions, lithium ions, calcium ions, magnesium ions, cesium ions, strontium ions, copper ions, cadmium ions, lead ions, thallium ions, and silver ions) and anions (such as fluorine ions, chlorine ions, iodine ions, thiocyanate ions, nitrite ions, monohydrogen phosphate ions, dihydrogen phosphate ions, perchlorate ions, nitrate ions, bromate ions, carbonate ions, acetate ions, and sulfate ions).

Where monomers having a self-organizing function are used, the monomers in an arrayed state are irradiated with an electron beam, thus inducing polymerization. This can enhance the selectivity with respect to a certain kind of ions. In order to enhance the orientation of a functional group, it may be necessary to insert a different monomer into the main chain of a polymer, for providing a distance at which a pendant functional group orients itself easily.

The monomer units, according to the present invention, can be oligomers if they contain unsaturated groups capable of becoming active species that induce a polymerization or bridging reaction when irradiated with an electron beam or radiation.

This electron beam-induced polymerization of monomers or monomer mixtures can take various forms, such as bulk polymerization and solution polymerization. For ease of operability of later process steps, it is desired to irradiate a liquid spread like a film 17 on a substrate with an electron beam. In the case of a liquid monomer, it is used intact. In the case of a solid monomer, it is necessary to liquefy it by adding a solvent or monomer necessary for the liquefaction or by heating. Preferably, the thickness of the liquid monomer or monomer mixture over the substrate is about 30 to 500 μm. No limitations are placed on the material of the substrate 18, as long as it can hold the monomer thereon. For example, the material of the substrate is glass, polyethylene, paraffin, or silicon. If possible, the monomer may be floated over water, oil, or the like.

Figure 3:
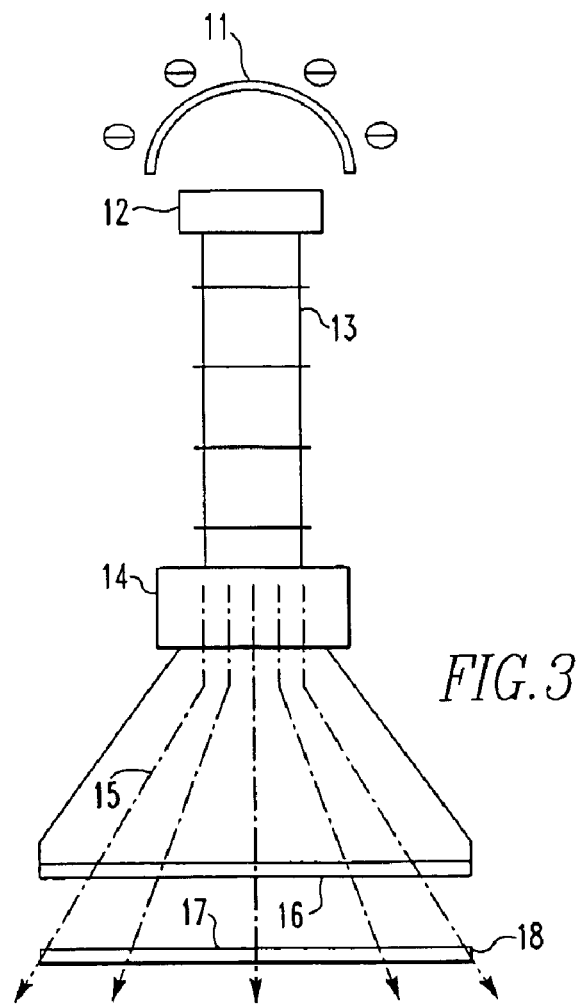
FIG. 3 is a schematic diagram of an electron beam irradiation system used in Examples 1 and 2 of the present invention.

An electron beam irradiation system is schematically shown in FIG. 3. This system includes an electron gun 12 placed within a vacuum. Electrons extracted from the gun 12 as an electron beam 15 are accelerated by an accelerating tube 13 and secondary scanning coils 14 and penetrated through titanium foil 16. Then, the beam is shot at a target 17 placed within a vacuum or ambient of an inert gas, such as nitrogen gas.

The electron beam is shot at a low accelerating voltage of less than 1,000 kV, more preferably, less than 300 kV. The dose of the electron beam is preferably 50 to 500 kGy, although the value varies depending on the treated monomer. With respect to the actual electron beam irradiation time, for the same dose of electron beam, the electron beam is shot at a relatively low energy for a long time in some cases and shot at a relatively high energy for a short time in other cases. To prevent production of excessive active species, such as radicals, the former method is desirable to obtain large molecular weights of uniform molecular weight distribution.

To polymerize monomers or monomer mixture on the substrate while preventing decomposition, the monomers are preferably kept cool even by forced cooling. Usually, the monomers are kept below room temperature. In the case of monomers giving rise to low reaction rates, they may be heated mildly to promote the reaction. In this case, the heating temperature is preferably below 50° C.

The monomers or monomer mixture on the substrate must be placed within a vacuum or ambient of an inert gas, such as nitrogen gas. The presence of oxygen will produce a radical source, which is undesirable for the electron beam-induced polymerization of the present invention.

The following nonlimiting examples are provided to further illustrate the present invention.

EXAMPLE 1

Substituted styrene monomers having pendant functional groups consisting of quaternary ammonium salts represented by Formulas 1 and 2, respectively, were synthesized by a known method.

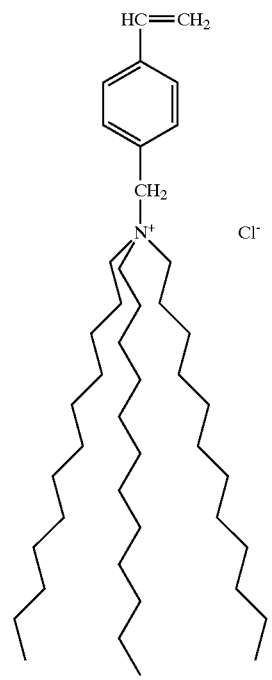

Formula 1

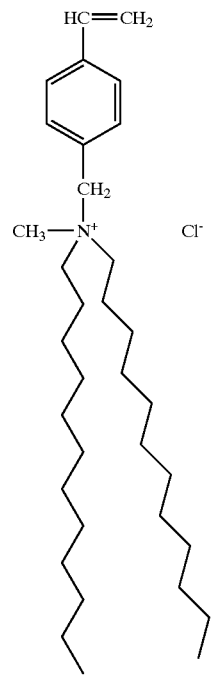

Formula 2

Then, 50 μl of each type of the synthesized liquid monomers was dripped onto the substrate by a micropipette. The dripped monomer was spread to a thickness of about 100 µm on the substrate. The monomer was irradiated with an electron beam by an electron beam irradiation system as shown in FIG. 3 in an ambient of nitrogen.

The energy conditions included an accelerating voltage of 150 kV and a filament current of 10 mA. The electron-beam dose per exposure was 100 kGy. The number of exposures was varied to vary the electron-beam dose to 100, 200, and 300 kGy. In this way, the state of each film formed on the substrate was examined. The results are given in Table 1.

TABLE 1

| Monomer | Formula 1 | | | Formula 2 | | |
|---|---|---|---|---|---|---|
| electron-beam dose (kgr) | 100 | 200 | 300 | 100 | 200 | 300 |
| substrate glass | x | . | . | x | . | . |
| polyethylene | x | . | . | x | x | . |
| paraffin | x | . | . | x | x | . |
| n-paraffin | x | . | . | x | x | . |
| silicon grease | x | . | . | x | x | . |

Films could be almost completely formed on every substrate with an electron-beam dose greater than 300 kGy. The total actual exposure time at electron-beam dose of 300 kGy was about 15 seconds.

The monomers represented by Formulas 1 and 2, respectively, were exposed on glass substrates with an electron beam at a dose of 300 kGy, producing solid polymer films P1 and P2, respectively.

The obtained solid polymer films P1 and P2 were subjected to dissolution testing. That is, they were allowed to stand at room temperature for 4 days. The results are shown in Table 2.

TABLE 2

| solvent | P1 | P2 |
|---|---|---|
| benzene | . | . |
| toluene | . | . |
| n-hexane | x | x |
| n-heptane | x | x |
| methanol | x | x |
| ethanol | x | x |
| acetone | . | . |
| methyl ethyl ketone | x | x |
| diethyl ether | x | x |
| tetrahydrofuran | . | . |
| dioxane | x | x |
| ethyl acetate | x | x |
| methylene chloride | x | x |
| chloroform | x | x |
| dimethyl formaldehyde | . | . |
| dimethylacetamide | . | . |
| dimethylsulfoxide | . | . |
| carbon tetrachloride | x | x |
| acetonitrile | x | x |

The results of the dissolution tests show that the films were insoluble to many solvents but the films swelled in some solvents. The films were dissolved in none of these solvents. It is estimated that the films are linear polymers which are either highly polymerized or considerably crosslinked.

Figure 4:
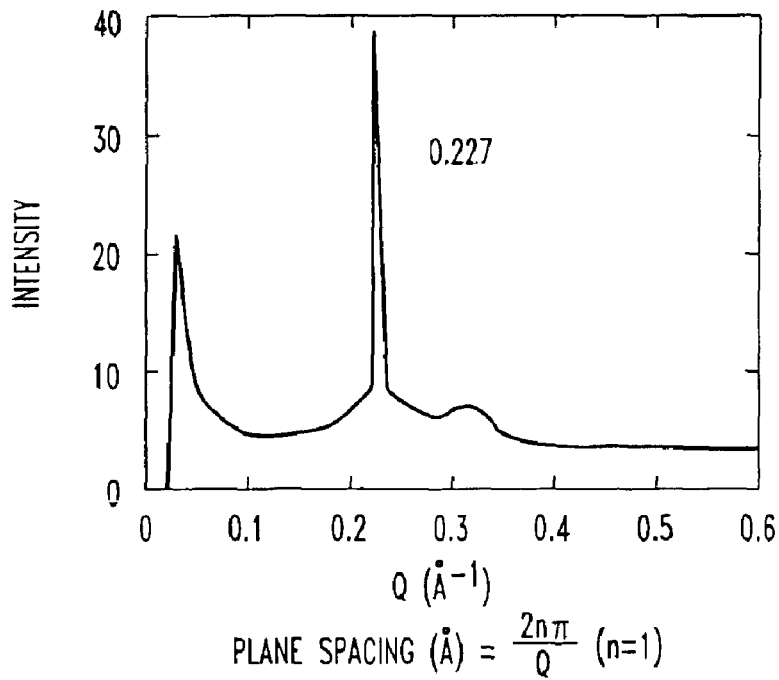
FIG. 4 is a chart illustrating the results of small-angle scattering measurements of synchrotron radiation emitted from a polymer film P1 produced in Example 1 of the present invention.
Figure 5:
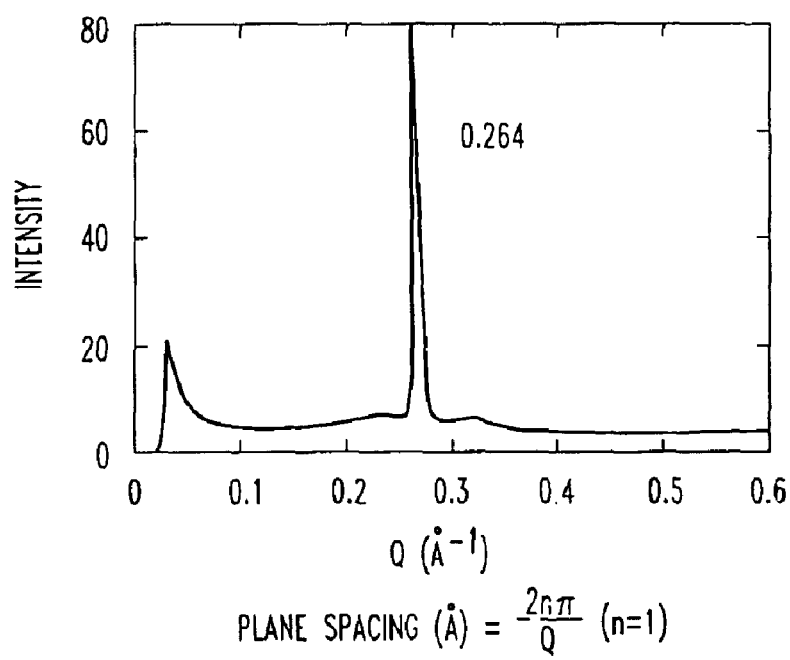
FIG. 5 is a chart illustrating the results of small-angle scattering measurements of synchrotron radiation emitted from a polymer film P2 produced in Example 1 of the present invention.

The materials represented by Formulas 1 and 2 are monomers having a self-organizing function. Small-angle scattering measurements of synchrotron radiation were performed on the films P1 and P2. Diffraction peaks were observed. Thus, it can be seen that the monomers have an arrayed structure (see FIGS. 4 and 5). The plane spacing of each of these polymers was calculated from these peaks. It has been found that each of these polymers consists of two orientations of molecules.

Figure 1:
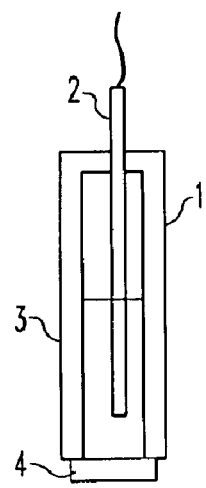
FIG. 1 is a cross-sectional view of a general ion sensor.
Figure 2:
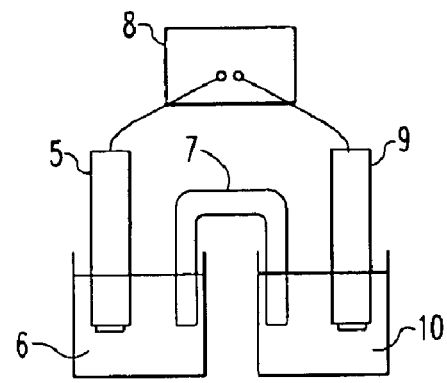
FIG. 2 is a schematic diagram of a general ion-measuring instrument.

These solid polymer films P1 and P2 were attached to the front end of the electrode body shown in FIG. 1, and potentiometric measurements were performed with the measuring instrument shown in FIG. 2. Aqueous solutions of sodium chloride of $10^{-1}$ M and $10^{-3}$ M, respectively, were used as sample liquids in the measurements. A potential gradient of about −58 mV/decade was observed for both P1 and P2. This value agrees well with a calculated value of −59 mV/decade found from the Nernst equation. Consequently, it is seen that the ion sensitive film has a sufficient sensitivity for an ion sensor.

EXAMPLE 2

Placed on a glass substrate was 2-allyloxymethyl-18-crown 6-ether (produced by Tokyo Kasei Kogyo Co., Ltd.) represented by Formula 3. This material was irradiated with an electron beam at an accelerating voltage of 150 kV, a filament current of 10 mA, and an electron-beam dose of 300 kGy, in the same way as in Example 1. In this manner, a solid polymer film P3 was prepared.

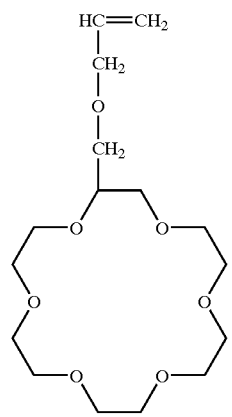

Formula 3

The obtained solid polymer film P3 was subjected to dissolution tests. That is, it was allowed to stand at room temperature for 4 days. The results are shown in Table 3.

TABLE 3

| solvent | P3 |
|---|---|
| benzene | . |
| toluene | . |
| n-hexane | x |
| n-heptane | x |
| methanol | x |
| ethanol | x |
| acetone | . |
| methyl ethyl ketone | x |
| diethyl ether | x |
| tetrahydrofuran | . |
| dioxane | x |
| ethyl acetate | x |
| methylene chloride | x |
| chloroform | x |
| dimethyl formaldehyde | . |
| dimethylacetamide | . |
| dimethylsulfoxide | . |

TABLE 3-continued

| solvent | P3 |
|---|---|
| carbon tetrachloride | x |
| acetonitrile | x |

The results of dissolution tests show that the polymers exhibited dissolution behaviors in the presence of various solvents, in exactly the same way as in Example 1. Again, it is estimated that the films are linear polymers which are either highly polymerized or considerably cross-linked.

In the same way as in Example 1, the solid polymer film P3 was attached to the front end of the electrode body, and potentiometric measurements were carried out. Aqueous solutions of sodium chloride of $10^{-1}$ M and $10^{-3}$ M, respectively, were used as sample liquids in the measurements. A potential gradient of about −55 mV/decade was observed. It is observed that the film also has a sufficient sensitivity for an ion sensor.

As described thus far, the present invention makes it possible to produce a long-lived ion sensitive film which is used in an ion sensor and has excellent durability, a high degree of polymerization, and a narrow range of molecular weights, by preparing a monomer mixture consisting chiefly of monomer units including a functional group having an identification function and a second group of bonded atoms capable of becoming an active species and by irradiating the monomer mixture with an electron beam or radiation in a low energy range to polymerize the monomer mixture. The active species induces a polymerization or bridging reaction by being irradiated with the electron beam or radiation.

Furthermore, the invention provides an ion sensitive film which is used in an ion sensor and can be directly produced from a film-like monomer or mixture without requiring refining, the film-like monomer reaching a high reaction rate in a quite short reaction time.

Additionally, in a monomer having a self-organizing function, the monomer can be polymerized in an arrayed state. This enhances the selectivity with respect to the ions to be identified.

Having thus described our invention with the detail and particularity required by the Patent Laws, what is desired protected by Letters Patent is set forth in the following claims.

What is claimed is:

1. A method of producing an ion sensitive film for an ion sensor, said method comprising the steps of:
    preparing a monomer mixture consisting chiefly of monomer units including a functional group having a function of identifying a certain chemical substance and a second group of bonded atoms capable of becoming an active species that induces one of a polymerization reaction and a bridging reaction by being irradiated with an electron beam or radiation, wherein said monomer units are maintained below room temperature; and
    irradiating said monomer mixture by the electron beam or radiation to polymerize the monomer mixture.

2. The method of claim 1, wherein said monomer units have a self-organizing function and induce a polymerization reaction by being irradiated with the electron beam, whereby the monomer units are polymerized.

3. A method of producing an ion sensitive film for an ion sensor, said method comprising the steps of:
    preparing a monomer mixture consisting chiefly of monomer units including a functional group having a function of identifying a certain chemical substance and a second group of bonded atoms capable of becoming an active species that induces one of a polymerization reaction and a bridging reaction by being irradiated with an electron beam or radiation; and
    irradiating said monomer mixture by the electron beam or radiation to polymerize the monomer mixture shot in a vacuum or ambient of inert gas.

4. A method of producing an ion sensitive film for an ion sensor, said method comprising the steps of:
    preparing a monomer mixture consisting chiefly of monomer units including a functional group having a function of identifying a certain chemical substance and a second group of bonded atoms capable of becoming an active species that induces one of a polymerization reaction and a bridging reaction by being irradiated with an electron beam; and
    irradiating said monomer mixture by the electron beam or radiation to polymerize the monomer mixture, said irradiating electron beam being accelerated by an accelerating voltage of less than 1,000 kV.

5. A method of producing an ion sensitive film for an ion sensor, said method comprising the steps of:
    preparing a monomer mixture consisting chiefly of monomer units including a functional group having a function of identifying a certain chemical substance and a second group of bonded atoms capable of becoming an active species that induces one of a polymerization reaction and a bridging reaction by being irradiated with an electron beam; and
    irradiating said monomer mixture by the electron beam or radiation to polymerize the monomer mixture, wherein the dose of said electron beam is in the range of from 50 to 500 kGy.

6. The method of claim 3, 4, or 5, wherein said monomer units react slowly, and wherein said monomer units are heated to a given temperature.

7. The method of claim 6, wherein said given temperature is below 50° C.

8. The method of claim 3, 4, or 5, wherein said functional group is one or more selected from the group consisting of functional groups having crown ether structure, valinomycin structure, calixarene structure, porphyrin structure, organotin structure, organomercuric structure, and cyclic polyamine structure, and ion-exchange groups.

9. The method of claim 3, 4, or 5, wherein said certain chemical substance is an ion species.

10. The method of claim 9, wherein said ion species is one or more species selected from the group consisting of cations including sodium ions, potassium ions, lithium ions, calcium ions, magnesium ions, cesium ions, strontium ions, copper ions, cadmium ions, lead ions, thallium ions, and silver ions.

11. The method of claim 9, wherein said ion species is one or more species selected from the group consisting of anions including fluorine ions, chlorine ions, iodine ions, thiocyanate ions, nitrite ions, monohydrogen phosphate ions, dihydrogen phosphate ions, perchlorate ions, nitrate ions, bromate ions, carbonate ions, acetate ions, and sulfate ions.

12. The method of claim 3, 4, or 5, wherein said monomer mixture is spread over a substrate and irradiated with said electron beam or radiation.

13. The method of claim 12, wherein said monomer mixture spread over the substrate has a thickness in the range of from 30 to 500 $\mu$m.

* * * * *